United States Patent
Lulo et al.

(10) Patent No.: US 6,544,225 B1
(45) Date of Patent: Apr. 8, 2003

(54) EMBOLIC COIL HYDRAULIC DEPLOYMENT SYSTEM WITH PURGE MECHANISM

(75) Inventors: Robert Lulo, Pembroke Pines, FL (US); Brett E. Naglreiter, Hollywood, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

(21) Appl. No.: 09/515,944

(22) Filed: Feb. 29, 2000

(51) Int. Cl.[7] ............................................. A61M 29/00
(52) U.S. Cl. .................. 604/104; 604/96.01; 606/191; 606/194
(58) Field of Search ................................ 604/104, 96.01, 604/102.01; 606/191, 194, 198, 200

(56) References Cited

U.S. PATENT DOCUMENTS

| | | |
|---|---|---|
| 2,853,070 A | 9/1958 | Julliard |
| 3,334,629 A | 8/1967 | Cohn |
| 3,353,718 A | 11/1967 | McLay |
| 3,635,223 A * | 1/1972 | Klieman .................... 128/348 |
| 4,512,338 A | 4/1985 | Balko et al. |
| 4,734,093 A | 3/1988 | Bonello et al. |
| 4,743,230 A | 5/1988 | Nordquest |
| 4,811,737 A | 3/1989 | Rydell |
| 4,832,692 A | 5/1989 | Box et al. |
| 4,906,241 A | 3/1990 | Noddin et al. |
| 4,919,121 A | 4/1990 | Rydell et al. |
| 4,938,220 A | 7/1990 | Mueller, Jr. |
| 4,994,069 A | 2/1991 | Ritchart et al. |
| 4,994,071 A | 2/1991 | MacGregor |
| 5,035,705 A | 7/1991 | Burns |
| 5,108,407 A | 4/1992 | Geremia et al. |
| 5,122,136 A | 6/1992 | Guglielmi et al. |
| 5,135,486 A | 8/1992 | Eberle et al. |
| 5,137,514 A | 8/1992 | Ryan |
| 5,167,624 A | 12/1992 | Butler et al. |
| 5,168,757 A | 12/1992 | Rabenau et al. |
| 5,201,754 A | 4/1993 | Crittenden et al. |
| 5,217,484 A | 6/1993 | Marks |
| 5,234,437 A | 8/1993 | Sepetka |
| 5,250,071 A | 10/1993 | Palermo |
| 5,261,916 A | 11/1993 | Engelson |
| 5,263,964 A | 11/1993 | Purdy |
| 5,304,195 A | 4/1994 | Twyford, Jr. et al. |

(List continued on next page.)

FOREIGN PATENT DOCUMENTS

| | | |
|---|---|---|
| EP | 0 717 969 | 6/1996 |
| EP | 0 739 607 | 10/1996 |
| WO | WO 96/02100 | 1/1996 |
| WO | WO 98/02100 | 1/1998 |

*Primary Examiner*—Ira S. Lazarus
*Assistant Examiner*—Tu Cam Nguyen

(57) ABSTRACT

A medical device for placing an embolic coil at a preselected location within a vessel comprising a positioning catheter having a distal section for retaining the embolic coil and an aperture for purging air from the device. The aperture is sized to allow air under fluid pressure to freely escape from within the catheter but to highly restrict the flow of more viscous fluids. At higher fluid pressures, the wall of the distal section expands outwardly to release the coil.

33 Claims, 2 Drawing Sheets

U.S. PATENT DOCUMENTS

| | | | |
|---|---|---|---|
| 5,312,415 A | 5/1994 | Palermo | |
| 5,334,210 A | 8/1994 | Gianturco | |
| 5,336,183 A | 8/1994 | Greelis et al. | |
| 5,342,304 A | 8/1994 | Tacklind et al. | |
| 5,350,397 A | 9/1994 | Palermo et al. | |
| 5,382,259 A | 1/1995 | Phelps et al. | |
| 5,403,292 A | 4/1995 | Ju | |
| 5,443,478 A | 8/1995 | Purdy | |
| 5,470,317 A | 11/1995 | Canazey et al. | |
| 5,534,007 A | 7/1996 | Germain et al. | |
| 5,551,954 A | 9/1996 | Buscemi et al. | |
| 5,578,074 A | 11/1996 | Mirigian | |
| 5,582,619 A | 12/1996 | Ken | |
| 5,601,600 A | 2/1997 | Ton | |
| 5,609,608 A | 3/1997 | Benett et al. | |
| 5,647,847 A | 7/1997 | Lafontaine et al. | |
| 5,669,931 A * | 9/1997 | Kupiecki et al. | 606/191 |
| 5,690,667 A | 11/1997 | Gia | |
| 5,711,909 A * | 1/1998 | Gore et al. | 264/320 |
| 5,728,065 A * | 3/1998 | Follmer et al. | 604/96 |
| 5,743,905 A * | 4/1998 | Eder et al. | 606/32 |
| 5,772,668 A | 6/1998 | Summers et al. | |
| 5,797,953 A * | 8/1998 | Tedulve | 606/200 |
| 5,800,454 A * | 9/1998 | Jacobsen et al. | 606/191 |
| 5,800,455 A * | 9/1998 | Palermo et al. | 606/191 |
| 5,817,057 A | 10/1998 | Berenstein et al. | |
| 5,853,418 A | 12/1998 | Ken et al. | |
| 5,989,242 A * | 11/1999 | Saadat et al. | 606/1 |
| 6,022,326 A * | 2/2000 | Zadno-Azizi et al. | 606/96 |
| 6,024,754 A * | 2/2000 | Angelson | 606/213 |
| 6,063,100 A * | 5/2000 | Diaz et al. | 606/191 |
| 6,068,644 A * | 5/2000 | Lulo et al. | 606/191 |
| 6,074,407 A * | 6/2000 | Levine et al. | 606/194 |
| 6,099,546 A * | 8/2000 | Gia | 606/191 |
| 6,113,622 A * | 9/2000 | Hieshima | 606/200 |
| 6,117,142 A * | 9/2000 | Goodson et al. | 606/108 |
| 6,149,664 A * | 11/2000 | Kurz | 606/194 |
| 6,165,178 A * | 12/2000 | Bashiri et al. | 606/108 |
| 6,183,491 B1 * | 2/2001 | Lulo | 606/191 |
| 6,190,373 B1 * | 2/2001 | Palermo et al. | 606/1 |
| 6,238,415 B1 * | 5/2001 | Sepetka et al. | 606/213 |
| 6,375,669 B1 * | 4/2002 | Rosenbluth et al. | 606/200 |
| 2001/0008976 A1 * | 7/2001 | Wang | 623/1.11 |

* cited by examiner

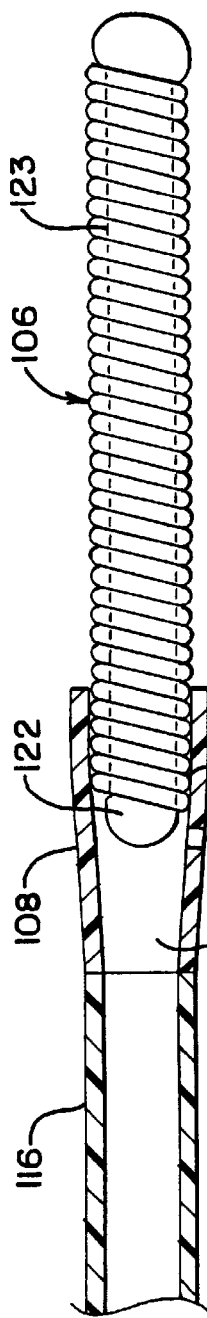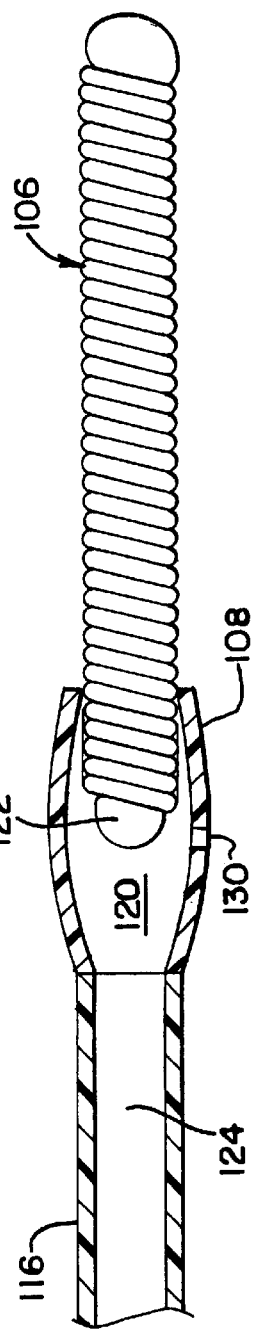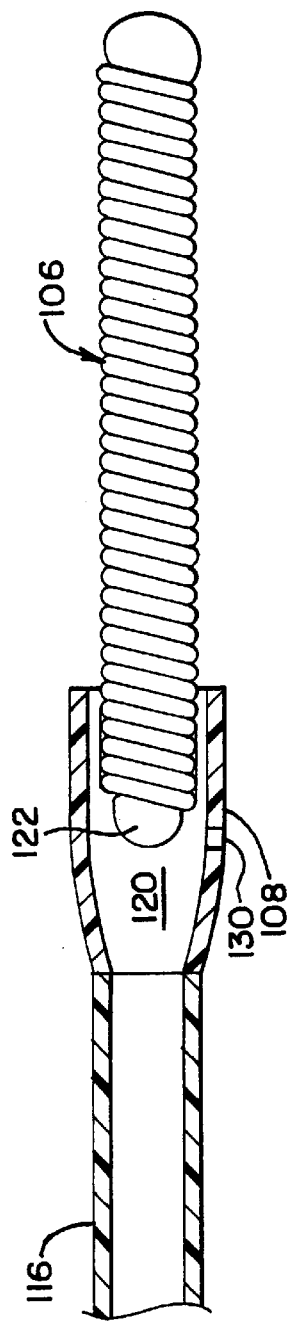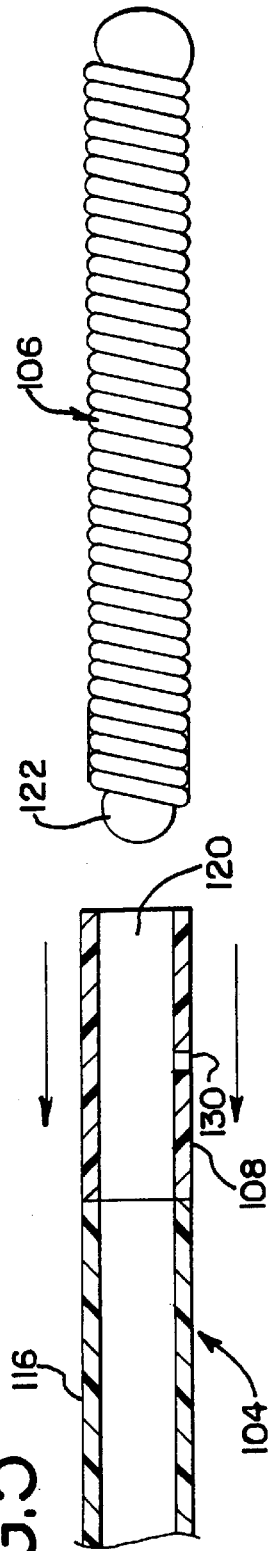

EMBOLIC COIL HYDRAULIC DEPLOYMENT SYSTEM WITH PURGE MECHANISM

BACKGROUND OF THE INVENTION

1. Field of the Invention

The present invention relates generally to a medical device for placing an embolic coil at a preselected location within a vessel of the human body. More particularly, the present invention relates to a catheter system having a distal tip for retaining an embolic coil in order to transport the coil to a preselected position within the vessel and a control mechanism for releasing the embolic coil at the preselected position.

2. Description of the Prior Art

For many years, flexible catheters have been used to place various devices within the vessels of the human body. Such devices include dilation balloons, radiopaque fluids, liquid medications, and various types of occlusion devices like balloons and embolic coils.

In the case of balloon catheters, prior to introducing the catheter into a human body, it is desirable to purge air from the catheter with a liquid to prevent the air from being introduced into blood vessels. In the past, purging the catheter involved inflating the balloon section of the catheter to allow the air to escape out of the distal end of the balloon and then providing some mechanism to prevent air from reentering the balloon while it is being deflated.

U.S. Pat. No. 5,728,065 to Follmer, et al., discloses a balloon catheter with a vent hole disposed near the distal end of the balloon. The vent hole normally lays against the surface of an inner tubular member, preventing gases from entering the balloon. During purging, the balloon is inflated, the distal end of the balloon opens exposing the vent hole, and gases and a portion of the inflation medium flow out.

U.S. Pat. No. 4,811,737 to Rydell, discloses a balloon catheter with a slit in the distal portion of the tubular member. Fluid is injected into the catheter and flows through multiple inflation ports to expand the balloon. The purging fluid forces the air within the balloon through the slit in the tubular member.

U.S. patent application Ser. No. 09/400,680 to Barry, et al., entitled, "Heated Vascular Occlusion Coil Deployment System," filed Sep. 21, 1999; U.S. patent application Ser. No. 09/399,714 to Barry, et al., entitled, "Embolic Coil Deployment System With Retaining Jaws," filed Sep. 21, 1999; U.S. patent application Ser. No. 09/177,848 to Hieshima, entitled, "Embolic Coil Hydraulic Deployment System," filed Oct. 21, 1998; U.S. patent application Ser. No. 09/256,161 to Lulo, entitled, "Embolic Coil Deployment System With Improved Embolic Coil," filed Feb. 22, 1999; U.S. patent application Ser. No. 09/256,163 to Diaz, et al., entitled, "Embolic Coil Deployment System With Improved Embolic Coil," filed Feb. 22, 1999; U.S. patent application Ser. No. 09/258,678 to Goodson, et al., entitled, "Embolic Coil Hydraulic Deployment System With Improved Syringe Injector," filed Feb. 25, 1999; and U.S. patent application Ser. No. 09/257,742 to Lulo, et al., entitled, "Embolic Coil Hydraulic Deployment System Having Improved Catheter," filed Feb. 24, 1999, are all assigned to the same assignee as the subject application and disclose embolic coil deployment systems for use in deploying an embolic device at a predetermined location within a vessel.

SUMMARY OF THE INVENTION

In accordance with the present invention, there is provided a vascular occlusive coil deployment system for use in placing a coil at a preselected site within a vessel including a catheter having a tubular wall and having a lumen extending throughout the length of the catheter. The catheter further includes a proximal section and a distal section. The distal section of the catheter is formed from a material which exhibits the characteristic that the wall of the distal section of the catheter expands outwardly when a liquid is applied within the lumen of the catheter. A syringe is coupled to the proximal section of the catheter for applying the liquid within the lumen of the catheter. The proximal end of an embolic coil is disposed in fluid-tight engagement within the lumen of the distal section of the catheter. When the liquid is applied within the lumen of the catheter, the wall of the distal section of the catheter expands outwardly and the proximal end of the embolic coil is released. At least one aperture is included for purging air from the lumen of the catheter to prevent the air from being introduced into the blood vessels. The aperture extends radially through the wall of the distal section of the catheter at a point proximal to the proximal end of the embolic coil. The aperture is sized such that air can pass through the aperture when fluid pressure is applied to the interior of the catheter but the flow of more viscous fluids is highly restricted.

In accordance with another aspect of the present invention, there is provided a vascular occlusive coil deployment system for use in placing a coil at a preselected site within a vessel including a catheter having a tubular wall and having a lumen extending throughout the length of the catheter. The catheter further includes a proximal section and a distal section. The distal section of the catheter is formed from a material which exhibits the characteristic that the wall of the distal section of the catheter expands outwardly when a liquid is applied within the lumen of the catheter. There is also provided a means for applying the liquid within the lumen of the catheter. The proximal end of an embolic coil is disposed in fluid-tight engagement within the lumen of the distal section of the catheter. When the liquid is applied within the lumen of the catheter, the wall of the distal section of the catheter expands outwardly, and the proximal end of the embolic coil is released. Finally, the vascular occlusive coil deployment system includes a means for purging air from the system.

In accordance with another aspect of the present invention, the means for applying a fluid pressure within the lumen of the catheter comprises a syringe coupled to the proximal section of the catheter.

In accordance with another aspect of the present invention, the purging means comprises at least one aperture extending radially through the wall of the distal section of the catheter at a point just proximal to the proximal end of the embolic coil.

In accordance with another aspect of the present invention, the aperture is sized such that the outflow is highly restricted for liquids having a viscosity greater than about $1 \times 10^{-8}$ lb·s/in$^2$.

In accordance with another aspect of the present invention, the aperture is sized such that the highly restricted outflow of liquid produces a fluid pressure within the lumen of the distal section of the catheter of at least 250 psi.

In accordance with another aspect of the present invention, the aperture is circular and has a diameter between approximately 0.00095 inches and 0.0012 inches. Preferably, the diameter is approximately 0.001 inches.

In accordance with another aspect of the present invention, the aperture is located between about 0.003 inches and 0.006 inches from the proximal end of the embolic coil.

In accordance with another aspect of the present invention, the liquid applied within the lumen of the catheter exerts a fluid pressure within the lumen of the proximal section of the catheter between about 50 psi and 125 psi and thereby causes air to pass through the aperture in the distal section of the catheter.

In accordance with still another aspect of the present invention, the proximal section of the catheter and the distal section of the catheter are formed from substances with different durometers. The distal section is formed from a material having a durometer which is substantially lower than the durometer of the material used to form the proximal section. The proximal section of the catheter is formed from a polymer having a durometer between 62 D to 75 D and the distal section of the catheter is formed from a polymer having a durometer between about 25 D and 55 D. Preferably, the proximal section of the catheter is formed from a material having a durometer of about 75 D and the distal section of the catheter is formed from a material having a durometer of about 40 D.

In accordance with another aspect of the present invention, the liquid is formed of saline solution. Preferably, the saline solution includes about 0.9% sodium chloride.

BRIEF DESCRIPTION OF THE DRAWINGS

FIG. 2 is an enlarged, partially sectioned view showing the distal end of the coil deployment system prior to deployment of the coil;

FIGS. 3 and 4 illustrate the sequential steps in the radial expansion of the distal tip of the coil deployment system as the embolic coil is released; and, FIG. 5 illustrates the distal tip of the coil deployment system after release of the embolic coil.

DESCRIPTION OF A PREFERRED EMBODIMENT

Figure 1:
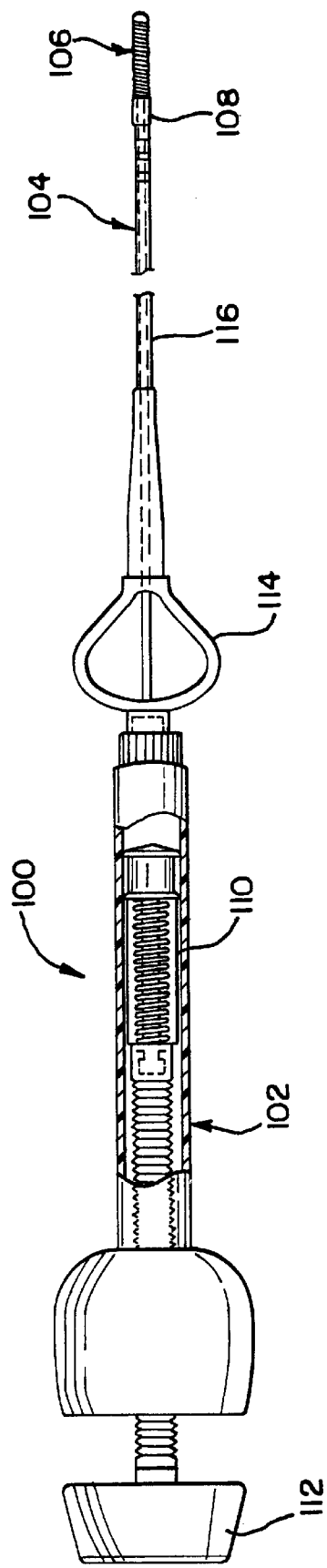
FIG. 1 is an enlarged, partially sectioned view of the hydraulic vascular occlusive coil deployment system of the present invention.

FIG. 1 generally illustrates the vascular occlusive coil deployment system 100 which is comprised of a catheter 104 having a proximal section 116 and a distal section 108, a syringe 102 coupled to the proximal section 116 of the catheter 104, and an embolic coil 106 partially disposed within the lumen of the distal section 108 of the catheter. As may be seen, the syringe 102 includes a threaded piston 110 that is controlled by a handle 112 for infusing fluid into the interior of the catheter 104. Also as illustrated, the catheter 104 includes a winged hub 114 that aids in the insertion of the catheter into the vascular system of the body.

FIG. 2 illustrates in more detail the distal section 108 of the catheter 104. A proximal end 118 of the embolic coil 106 is disposed within the distal section 108 of the catheter 104 and is tightly held within the lumen 120 of this distal section 108 prior to the release of the coil. As may be appreciated, FIG. 2 illustrates the vascular occlusive coil deployment system prior to activation of the piston of the syringe and prior to release of the coil.

The embolic coil 106 may take various forms and configurations and may even take the form of a randomly wound coil. With the helically wound coil as illustrated in FIG. 2, the coil is provided with a weld bead or seal plug 122 which is disposed in a lumen 123 which, extends throughout the length of the coil 106. In addition, adjacent turns at the proximal end 118 of the coil 106 are welded together so that the welded turns of the coil in conjunction with the seal plug 122 provide a generally unitary structure. When the coil 106 is placed in fluid-tight engagement with the lumen 120 of the catheter 104, the seal plug 122 serves to prevent the flow of fluid through the lumen 123 of the coil 106.

A small circular aperture 130 is located just proximal to the seal plug 122 and extends radially through the wall of the distal section 108 of the catheter. The aperture 130 provides a means for purging the catheter 104 of air prior to inserting the catheter into a patient. The aperture 130 is sized such that fluids with a viscosity less than about $1 \times 10^{-8}$ lb·s/in² will exit the catheter 104 at low pressures during purging, but fluids with a viscosity greater than about $1 \times 10^{-8}$ lb·s/in² will have a restricted outflow so that sufficient fluid pressure can be built up in the distal section of the catheter to release the coil during coil deployment. For example, the flow of air, having a viscosity of about $2.6 \times 10^{-9}$ lb·s/in², would meet little resistance during purging while the flow of saline solution, having a viscosity of about $1.74 \times 10^{-\partial}$lb·s/in², would be highly restricted. This highly restricted outflow allows the fluid pressure within the catheter to reach a deployment pressure of about 250 psi at the distal section. Typically, the purge pressure, measured at the proximal section of the catheter, is in the range of about 50 psi to 125 psi, with about 90 psi to 110 psi being the preferred range.

Purging the catheter takes up to 60 seconds using saline solution of 0.9% sodium chloride. More viscous solutions may be used, but will take longer to purge the catheter of air. For optimum operation of the vascular occlusive coil deployment system, the purging solution should preferably have a viscosity of about $1.74 \times 10^{-7}$ lb·s/in².

As can be appreciated, the aperture 130 should be located as close to the seal plug 122 as possible to allow as much air as possible to be purged from the lumen 120 of the catheter 104. Elevation of the distal section during purging is not necessary. In the preferred embodiment, the aperture has a diameter in the range between about 0.00095 inches to 0.0012 inches, with approximately 0.001 inches being preferred, and is formed using a heated wire. The aperture is located approximately 0.003 inches to 0.006 inches from the seal plug.

As can be appreciated, the small geometry of the catheter results in a loss in fluid pressure between the proximal section and the distal section. This loss, due primarily to the restricted flow of fluid through the small inner diameter of the catheter and the smaller purge hole in the distal section, is on the order of about 25%. To further complicate matters, accurate measurements of the pressure delivered to the distal section are difficult to measure. Thus, actual pressure measurements can be taken at the proximal section of the catheter, while the pressure delivered to the distal section must be calculated. For example, the deployment pressure, measured at the proximal section, is typically in the range of about 150 psi to 565 psi, with about 400 psi being preferred. The actual deployment pressure applied at the distal end must be calculated and is expected to be in the range of about 110 psi to 425 psi, with 250 psi being preferred.

FIGS. 3 and 4 generally illustrate the coil release mechanism in action for the vascular occlusive coil deployment system. More particularly, as shown in FIG. 3, when a hydraulic pressure is applied to an interior 124 of the catheter 104 the relatively low durometer distal section 108 of the catheter begins to expand outwardly. As the distal section 108 continues to expand there comes a point as illustrated in FIG. 4 in which the coil 106 becomes disengaged from the lumen of the distal section 108 and the coil is then released from the catheter and is deployed at that location within the vessel.

As illustrated in FIG. 5, when the coil 106 has been released from the catheter 104 the catheter may then be withdrawn leaving the coil positioned at the desired site.

In the preferred embodiment, the proximal section 116 and the distal section 108 of the catheter 104 are formed of materials having different durometers. As may be appreciated, there are numerous materials that could be used to fabricate the proximal section 116 and distal section 108 of the catheter 104. The proximal section 116 is preferably formed from Vestimid material having a durometer in a range of about 62 D to 75 D, with a durometer of 75 D being preferred. This allows the proximal section to be sufficiently flexible to transverse the to vasculature of the human body, but sufficiently rigid to resist any outward expansion of the walls when a fluid pressure of approximately 250 psi is applied to the interior of the distal section of the catheter.

The distal section 108 of the catheter is preferably formed from polymer material with a relatively low durometer. Low durometer polymer materials typically exhibit the characteristic of expanding when a fluid pressure is applied to the interior of the catheter. In the preferred embodiment, when a fluid pressure of between about 150 psi and 565 psi is applied to the interior of the proximal section of the catheter, the walls of the distal section 108 expand outwardly and thereby release the proximal end 118 of the coil 106. In this embodiment, the distal section 108 is preferably formed from a block copolymer, such as Pebax material, having a durometer of between 25 D and 55 D, with a durometer of 40 D being preferred. As is well known to the art, heat bonding materials with significantly different durometers is typically achieved by bonding interposed layers of material with similar durometers. In the preferred embodiment, the proximal layer, with a durometer of 75 D, is bonded to an interposed layer of material (not shown) with a durometer of 55 D. The distal layer, with a durometer of 40 D, is then bonded to the layer of 55 D material.

With the vascular occlusive coil deployment system, it is possible to place an embolic coil very precisely at a desired location within a vessel. Once the coil has been positioned into the desired location by use of the catheter, the coil may be deployed by applying a fluid pressure to the interior of the catheter to thereby cause the catheter to release the coil and deposit the coil very accurately at the desired location.

As is apparent, there are numerous modifications of the preferred embodiment described above that will be readily apparent to one skilled in the art. These include variations and modifications of the coil, including numerous coil-winding configurations or other types of implant devices, such as a vascular filter. Also, there are obviously variations of the syringe arrangement for applying a fluid pressure to the interior of the catheter, including a hydraulic injector, pump, and other fluid-pressure generating systems. Additionally, there are variations of the number and type of purging means, including one or more elliptical holes or slits. These modifications would be apparent to those having ordinary skill in the art to which this invention relates and are intended to be within the scope of the claims that follow.

That which is claimed is:

1. A vascular occlusive coil deployment system comprising:
   a catheter having a tubular wall and having a lumen extending throughout the length of the catheter, said catheter further having a proximal section and a distal section, said distal section of the catheter being formed from a material which exhibits the characteristic that the wall of the distal section of the catheter expands outwardly when a liquid is applied within the lumen of the catheter;
   a syringe coupled to said proximal section of the catheter for applying the liquid within the lumen of the catheter;
   an embolic coil having a proximal end and a distal end, said proximal end of the embolic coil being disposed in fluid-tight engagement within said lumen of the distal section of the catheter, said proximal end of the embolic coil being released when the liquid is applied within the lumen of the catheter and the wall of the distal section of the catheter expands outwardly; and,
   at least one aperture for purging air from said lumen of the catheter, said aperture extending radially through said wall of the distal section of the catheter at a point proximal to the proximal end of the embolic coil.

2. A vascular occlusive coil deployment system as defined in claim 1, wherein said aperture is sized such that an outflow of liquid is highly restricted for liquids having a viscosity greater than about $1 \times 10^{-8}$ lb·s/in$^2$.

3. A vascular occlusive coil deployment system as defined in claim 1, wherein said aperture is sized such that the highly restricted outflow of liquid produces a fluid pressure within the lumen of the distal section of the catheter of about 250 psi.

4. A vascular occlusive coil deployment system as defined in claim 1, wherein said aperture is circular and has a diameter between approximately 0.00095 inches and 0.0012 inches.

5. A vascular occlusive coil deployment system as defined in claim 4, wherein said aperture is circular and has a diameter of approximately 0.001 inches.

6. A vascular occlusive coil deployment system as defined in claim 4, wherein said aperture is located between about 0.003 inches and 0.006 inches from said proximal end of the embolic coil.

7. A vascular occlusive coil deployment system as defined in claim 6, wherein said liquid applied within the lumen of the catheter exerts a fluid pressure within the lumen of the proximal section of the catheter between about 50 psi and 125 psi and thereby causes air to pass through the aperture in the distal section of the catheter.

8. A vascular occlusive coil deployment system as defined in claim 7, wherein said proximal section of the catheter and said distal section of the catheter are formed from materials with different durometers, said distal section being formed from a material having a durometer which is substantially lower than the durometer of the material used to form said proximal section.

9. A vascular occlusive coil deployment system as defined in claim 8, wherein said proximal section of the catheter is formed from a polymer having a durometer between 62 D to 75 D and said distal section of the catheter is formed from a polymer having a durometer of between about 25 D and 55 D.

10. A vascular occlusive coil deployment system as defined in claim 9, wherein said proximal section of the catheter is formed from a material having a durometer of about 75 D and the distal section of the catheter is formed from a material having a durometer of about 40 D.

11. A vascular occlusive coil deployment system as defined in claim 8, wherein said liquid comprises a saline solution.

12. A vascular occlusive coil deployment system as defined in claim 11, wherein said saline solution is comprised of about 0.9% sodium chloride.

13. A vascular occlusive coil deployment system comprising:
- a catheter having a tubular wall and having a lumen extending throughout the length of the catheter, said catheter further having a proximal section and a distal section;
- a syringe for applying a liquid within the lumen of the catheter;
- an embolic coil having a proximal end and a distal end, said proximal end of the embolic coil being disposed in fluid-tight engagement within said lumen of the distal section of the catheter, said proximal end of the embolic coil being released when the liquid is applied within the lumen of the catheter and the wall of the distal section of the catheter expands outwardly; and,
- an aperture extending radially through said wall of the distal section of the catheter at a point just proximal to the proximal end of the embolic coil.

14. A vascular occlusive coil deployment system as defined in claim 13, wherein said aperture is sized such that an outflow of liquid is highly restricted for liquids having a viscosity greater than about $1 \times 10^{-8}$ lb·s/in$^2$.

15. A vascular occlusive coil deployment system as defined in claim 13, wherein said aperture is sized such that the highly restricted outflow of liquid produces a fluid pressure within the lumen of the distal section of the catheter of at least 250 psi.

16. A vascular occlusive coil deployment system as defined in claim 13, wherein said aperture is circular and has a diameter between approximately 0.00095 inches and 0.0012 inches.

17. A vascular occlusive coil deployment system as defined in claim 16, wherein said aperture is circular and has a diameter of approximately 0.001 inches.

18. A vascular occlusive coil deployment system as defined in claim 16, wherein said aperture is located between about 0.003 inches and 0.006 inches from said proximal end of the embolic coil.

19. A vascular occlusive coil deployment system as defined in claim 18, wherein said liquid applied within the lumen of the catheter exerts a fluid pressure within the lumen of the proximal section of the catheter between about 50 psi and 125 psi and thereby causes air to pass through an aperture in the distal section of the catheter.

20. A vascular occlusive coil deployment system as defined in claim 19, wherein said proximal section of the catheter and said distal section of the catheter are formed from materials with different durometers, said distal section being formed from a material having a durometer which is substantially lower than the durometer of the material used to form said proximal section.

21. A vascular occlusive coil deployment system as defined in claim 20, wherein said proximal section of the catheter is formed from a polymer having a durometer between 62 D to 75 D and said distal section of the catheter is formed from a polymer having a durometer of between about 25 D and 55 D.

22. A vascular occlusive coil deployment system as defined in claim 21, wherein said proximal section of the catheter is formed from a material having a durometer of about 75 D and the distal section of the catheter is formed from a material having a durometer of about 40 D.

23. A vascular occlusive coil deployment system as defined in claim 21, wherein said liquid comprises a saline solution.

24. A vascular occlusive coil deployment system as defined in claim 23, wherein said saline solution is comprised of about 0.9% sodium chloride.

25. A medical device deployment system comprising:
- a catheter having a tubular wall and having a lumen extending throughout the length of the catheter, said catheter further having a proximal section and a distal section;
- a syringe for applying a liquid within the lumen of the catheter;
- a medical device having a proximal end and a distal end, said proximal end of the medical device being disposed in fluid-tight engagement within said lumen of the distal section of the catheter, said proximal end of the medical device being released when the liquid is applied within the lumen of the catheter; and,
- an aperture extending radially through said wall of the distal section of the catheter at a point just proximal to the proximal end of the medical device.

26. A medical device deployment system as defined in claim 25, wherein said aperture is sized such that an outflow of liquid is highly restricted for liquids having a viscosity greater than about $1 \times 10^{-8}$ lb·s/in$^2$.

27. A medical device deployment system as defined in claim 25, wherein said aperture is sized such that the highly restricted outflow of liquid produces a fluid pressure within the lumen of the distal section of the catheter of at least 250 psi.

28. A medical device deployment system as defined in claim 25, wherein said aperture is circular and has a diameter between approximately 0.00095 inches and 0.0012 inches.

29. A medical device deployment system as defined in claim 28, wherein said aperture is circular and has a diameter of approximately 0.001 inches.

30. A medical device deployment system as defined in claim 28, wherein said aperture is located between about 0.003 inches and 0.006 inches from said proximal end of the embolic coil.

31. A medical device deployment system as defined in claim 30, wherein said liquid applied within the lumen of the catheter exerts a fluid pressure within the lumen of the proximal section of the catheter between about 50 psi and 125 psi and thereby causes air to pass through the aperture in the distal section of the catheter.

32. A medical device deployment system as defined in claim 31, wherein said proximal section of the catheter and said distal section of the catheter are formed from materials with different durometers, said distal section being formed from a material having a durometer which is substantially lower than the durometer of the material used to form said proximal section.

33. A medical device deployment system as defined in claim 32, wherein said proximal section of the catheter is formed from a polymer having a durometer between 62 D to 75 D and said distal section of the catheter is formed from a polymer having a durometer of between about 25 D and 55 D.

* * * * *